United States Patent [19]

Musselman et al.

[11] Patent Number: 4,781,982

[45] Date of Patent: Nov. 1, 1988

[54] SURFACE TREATING MINERAL PARTICLES TO REDUCE HALIDE ADSORPTION

[75] Inventors: Lawrence L. Musselman; Larry F. Wieserman, both of Apollo, Pa.

[73] Assignee: Aluminum Company of America, Pittsburgh, Pa.

[21] Appl. No.: 126,244

[22] Filed: Nov. 27, 1987

[51] Int. Cl.$^4$ ............... A61K 7/18; B05D 7/00; B32B 5/16
[52] U.S. Cl. .................... 428/403; 106/417; 106/469; 106/483; 106/465; 106/486; 106/463; 424/49; 424/52; 427/215; 427/397.8; 428/404; 523/216; 524/437
[58] Field of Search ............ 106/308 B; 427/215, 427/397.8; 428/404, 403; 424/49, 52; 523/216; 524/437

[56] References Cited

U.S. PATENT DOCUMENTS

| | | | |
|---|---|---|---|
| 3,420,691 | 1/1969 | Thomas et al. | 428/404 X |
| 4,046,872 | 9/1977 | Mitchell et al. | 424/52 |
| 4,075,317 | 2/1978 | Mitchell et al. | 424/52 |
| 4,098,878 | 7/1978 | Baines et al. | 424/52 |
| 4,152,417 | 5/1979 | Mitchell et al. | 424/49 |
| 4,182,799 | 1/1980 | Rodish | 521/98 |
| 4,334,933 | 6/1982 | Abe et al. | 106/308 B |

*Primary Examiner*—Michael R. Lusignan
*Attorney, Agent, or Firm*—Glenn E. Klepac

[57] ABSTRACT

Mineral particles are surface treated with an alkali metal silicate, hydrogen peroxide, an acid, or an organophosphorus compound. A preferred surface treating method utilizes sodium silicate in aqueous solution at pH greater than 9, followed by neutralization with acid to precipitate a silica coating onto surface portions of the particles. The mineral particles are preferably alumina particles. The surface-treated alumina particles may be incorporated into fluoride dentifrices or compounded with halogenated hydrocarbons and polymeric resins to form flame-retardant polymer compounds.

20 Claims, No Drawings

SURFACE TREATING MINERAL PARTICLES TO REDUCE HALIDE ADSORPTION

FIELD OF THE INVENTION

The present invention relates to the surface treatment of mineral particles in order to reduce their adsorption of halide ions and halide free radicals.

BACKGROUND OF THE INVENTION

Alumina hydrate is a known adsorbent for several different halide ions and free radicals, including fluoride ions in aqueous solutions and fluoride, chloride, bromide, and iodide free radicals. When alumina hydrate is added to fluoride-containing dentifrices as a dental abrasive, untreated alumina hydrate particles will adsorb fluoride ions, thereby reducing fluoride concentration. It is thought that such reduction of fluoride concentration has a detrimental effect on caries prevention.

In Baines et al U.S. Pat. No. 4,098,878, there is disclosed a toothpaste containing alumina trihydrate abrasive particles which have been surface-treated with a long chain fatty acid or a mixture of such acids, or the corresponding alkali metal salt of such acids or mixtures. A preferred formulation relies upon surface treatment with stearic acid dissolved in acetone. Although this formulation successfully maintains an adequate fluoride ion concentration, the stearic acid is difficult to apply uniformly and may have an adverse taste if supplied in excessive amount.

In the prior art, sodium silicate has been added to dental cream compositions containing alumina abrasive material for the purpose of rendering the dental cream compatible with an unlined aluminum container. However, the pH conditions of sodium silicate addition were inadequate to prevent substantial reduction in luoride concentration by adsorption onto surface portions of the alumina. Dental cream compositions including both alumina and sodium silicate are disclosed in Mitchell et al U.S. Pat. Nos. 4,046,872; 4,075,317; and 4,152,417.

In another aspect of the present invention, alumina hydrate and halogenated hydrocarbon compounds are both known fire-retardant additives for flammable plastic resins. For example, Rodish U.S. Pat. No. 4,182,799 claims a flame-retarding additive for foamed polystyrene comprising 40-56 wt. % halogenated hydrocarbon, 16-23 wt. % alumina hydrate, 9-15 wt. % antimony oxide, and 14-22 wt. % zinc borate. The halogenated hydrocarbon inhibits flaming of the foamed polystyrene by generating halide-containing free radicals upon heating. However, alumina hydrate is a known adsorbent for such free radicals. Accordingly, there is a need to treat the alumina hydrate to reduce its adsorption of halide free radicals without affecting fire-retardancy of the hydrate.

It is a principal object of the present invention to provide a method for surface treating mineral particles that reduces adsorption of halide ions and halide free radicals onto surface portions of the particles. The mineral particles are preferably alumina particles.

A related object of the present invention is to provide alumina particles that are surface treated to reduce their adsorption of halide ions and halide free radicals.

Additional objects and advantages of the present invention will become apparent to persons skilled in the art from the following detailed description of our invention.

SUMMARY OF THE INVENTION

In accordance with the present invention, there is provided a method for surface treating mineral particles to reduce adsorption of halide ions and halide free radicals onto surface portions of the particles. The mineral may be alumina, bauxite, magnesia, mica, talc, hydrated calcium silicate, kaolin, hydrotalcite, calcium carbonate, magnesium carbonate, calcium phosphate, or sodium phosphate. The invention is particularly applicable to particles of alumina in various forms, including alpha alumina, although alumina hydrate is preferred. As used herein, the term "alumina hydrate" refers to $Al_2O_3 \cdot xH_2O$, where x varies from 1 to 3; in other words, the water of hydration varies between about 15 and 34.6% by weight of the alumina hydrate as determined by drying and then calcining at 1100° C. (2012° F.) for four hours. The expression "alumina trihydrate" refers to $Al_2O_3 \cdot 3H_2O$ or $Al(OH)_3$, also called "aluminum hydroxide". Alumina hydrate which is treated in accordance with the present invention can be obtained from several different sources, most commonly as a product of the well-known Bayer process.

The particles are generally alumina trihydrate particles having an average particle size of about 0.1–200 microns, preferably about 1–30 microns and more preferably about 1–10 microns. The invention has greater utility with smaller particle sizes of less than about 30 microns because halide surface adsorption is greater with the smaller sized particles.

The alumina hydrate particles are surface treated with a solution of surface treating agent which may be an alkali metal silicate, hydrogen peroxide, an acid or an organophosphorus compound. The particles are surface treated by mixing with a solution of the surface treating agent, adjusting the pH of the solution, separating the particles from the solution, and then drying the surface-treated particles at an elevated temperature. The surface treating agent is preferably applied in an aqueous solution.

The alkali metal silicate is preferably potassium silicate or sodium silicate. Aqueous solutions containing about 0.3–5 wt. % sodium silicate are preferred. The sodium silicate solution has an initial pH of at least 8.5. The solution pH is generally greater than 9 and preferably greater than 10. After the sodium silicate solution is neutralized, a very thin silica layer forms on the particles. The dried surface-treated particles contain less than about 0.2 wt. % (2,000 ppm) silica surface coating, remainder alumina.

Some suitable acids for inhibiting halide adsorption are hydrochloric acid, acetic acid, phosphoric acids, phosphonic acids, and phosphinic acids. Hydrochloric acid is preferred.

The organophosphorus compound may be an organophosphonate having the formula $RPO(OH)_2$ wherein R is a $C_1$–$C_{30}$ hydrocarbon group. The organophosphorus compound may also be an organophosphinate having the formula $RR'PO(OH)$ wherein R is as defined above, and R' is hydrogen or a $C_1$–$C_{30}$ hydrocarbon group. R is preferably a $C_{10}$–$C_{20}$ alkyl group. The $C_1$–$C_{30}$ alkyl esters of such organophosphonates and organophosphinates are also suitable. Some other suitable organophosphorus compounds are mono- and diesters of phosphoric acid. The phosphate monoesters have the formula $ROPO(OH)_2$ and the diesters have the formula $(RO)_2PO(OH)$, where R is defined above.

The surface-treated alumina is useful as a flame-retardant additive in polymer compounds and as a dental abrasive in fluoride toothpaste. One suitable polymer compound comprises about 100 parts by weight polymeric resin, about 1–400 parts by weight surface-treated alumina hydrate particles having average particle size of about 0.1–200 microns and about 5–50 parts by weight of a halogenated hydrocarbon. The resin may be thermoplastic, thermosetting, or elastomeric. Some suitable thermoset resins are unsaturated polyesters, epoxies, polyurethanes, and mixtures thereof. Some suitable elastomers are chlorinated polyethylene, styrene butadiene rubber, natural rubber, and mixtures thereof. The resin is preferably a thermoplastic resin which may be polystyrene, polypropylene, polyethylene, polyvinyl chloride or mixtures or copolymers thereof. Polystyrene is preferred. The alumina hydrate particles are preferably alumina trihydrate particles having average particle size of about 0.5–75 microns. The halogenated hydrocarbon is preferably a chlorinated wax, a brominated or chlorinated aliphatic or aromatic fire retardant. The polymer compound may also contain other flame-retardant additives such as metal oxides, halides, phosphates, and borates. Two particularly preferred additives are antimony oxide and zinc borate.

A fluoride dentifrice made with alumina hydrate surface treated by the method of our invention comprises about 30–98 wt. % of vehicle having a pH of about 5–8, about 2–70 wt. % alumina hydrate particles, and about 0.01–2 wt. % dissolved fluoride ion. The vehicle is preferably an aqueous slurry having a pH of about 5–7. In addition to water, the vehicle may contain humectants, thickeners, flavoring agents, sweeteners, and detergents. Glycerine is a suitable humectant, carboxymethyl cellulose and hydroxyethyl cellulose are suitable thickeners and sodium saccharinate is a useful sweetener. Although alumina hydrate may be the sole abrasive, it may also be combined with another abrasive such as calcium carbonate, magnesium carbonate, hydrotalcite, calcium or sodium phosphates or silica in various forms. The alumina hydrate particles preferably have an average particle size of about 1–20 microns, more preferably about 5–15 microns. One example is alumina trihydrate sold by Aluminum Company of America under the trademark C-333 and having an average particle size of about 8.5–10.5 microns. A more preferred alumina is precipitated in this size range to have very low surface area, preferably less than about 1 $m^2/g$. A particularly preferred alumina trihydrate has only about 0.4 $m^2/g$ surface area. The fluoride ion is supplied by water-soluble fluoride compounds such as sodium fluoride, stannous fluoride, ammonium fluoride, alkali-metal monofluorophosphates or mixtures thereof. The toothpaste preferably contains about 0.1 wt. % fluoride ion supplied by sodium fluoride.

DETAILED DESCRIPTION OF A PREFERRED EMBODIMENT

In a preferred embodiment of the present invention, 200 parts by weight of alumina trihydrate powder were mixed with 400 parts by weight of a 1 wt. % sodium silicate solution. The alumina trihydrate had an average particle size of about 10 microns. The solution had a pH of about 10.5. The solution was then neutralized by addition of hydrochloric acid, with adjustment of the pH to 6.0. After the pH was stabilized, the sample was filtered and dried at 150° C.

A series of tests was performed to determine effect of the surface treatment of the invention on adsorption of fluoride ion from aqueous sodium fluoride solution. Samples of treated and untreated alumina trihydrate were mixed with a solution containing 1,000 ppm fluoride ion and free fluoride content was of the tests are shown in Table I.

TABLE I

| Fluoride Adsorption After 18 Hours | |
|---|---|
| Surface Treatment | Fluoride Adsorption (% of original) |
| 1. Control (Not Treated) | 25% |
| 2. Hydrogen Peroxide | 9 |
| 3. Hydrochloric Acid | 8 |
| 4. Sodium Silicate | 3 |
| 5. Acetic Acid | 12 |
| 6. Phosphoric Acid | 15 |

The test results summarized above demonstrate that surface treatment with aqueous sodium silicate solution under the specific pH conditions claimed herein greatly reduces adsorption of fluoride ion onto surface portions of the alumina particles.

The foregoing description of our invention has been made with reference to some preferred embodiments. Persons skilled in the art will understand that numerous changes and modifications can be made therein without departure from the spirit and scope of the following claims. For example, the two specific fields of use described above are fluoride-containing dentifrices having alumina abrasive particles and polymer compounds containing a combination of alumina and chlorinated hydrocarbon fire-retardants. The invention is also applicable to other situations wherein it is desirable to reduce adsorption by alumina of fluoride, chloride, bromide, or iodide ions and free radicals.

What is claimed is:

1. A method for surface treating particles of a mineral to reduce adsorption of halide ions and halide free radicals onto surface portions of the particles, said method comprising:
    (a) surface treating mineral particles with an alkali metal silicate surface treating agent in an aqueous solution having an initial pH of at least 8.5;
    (b) neutralizing the aqueous solution to a pH of about 5–7, thereby to precipitate a silica coating onto surface portions of the particles;
    (c) separating the surface-treated mineral particles from the solution; and
    (d) drying the surface-treated particles.

2. The method of claim 1 wherein said mineral is selected from the group consisting of alumina, bauxite, magnesia, mica, talc, hydrated calcium silicate, kaolin, hydrotalcite, calcium carbonate, magnesium carbonate, calcium phosphate, and sodium phosphate.

3. The method of claim 1 wherein said mineral is alumina hydrate.

4. The method of claim 1 wherein said solution contains about 0.3–5 wt. % sodium silicate or potassium silicate.

5. The method of claim 1 wherein said aqueous solution has an initial pH greater than 9.

6. The method of claim 1 wherein said particles have an average particle size of about 0.1–200 microns.

7. The method of claim 1 wherein said particles have an average particle size of about 1–30 microns.

8. The method of claim 1 wherein said particles are alumina trihydrate particles having average particle size of about 5–20 microns and less than about 1 m²/g surface area.

9. Alumina trihydrate particles surface-treated by the method of claim 1 and having reduced affinity for halide ions and free radicals.

10. Alumina trihydrate particles surface-treated by the method of claim 1, said particles having an average particle size of about 5–20 microns.

11. Alumina particles having an average particle size of less than about 30 microns and reduced affinity for halide ions and free radicals, said particles being surface-treated by the method of claim 1.

12. Alumina particles surface-treated by the method of claim 1, said particles being coated with less than about 0.2 wt. % silica.

13. A polymer composition comprising:
   (a) about 100 parts by weight of a polymeric resin;
   (b) about 1–400 parts by weight alumina hydrate particles having an average particle size of about 0.1–200 microns, said particles being surface-treated by the method of claim 1, and
   (c) about 5–50 parts by weight of a halogenated hydrocarbon.

14. The polymer composition of claim 13 wherein said resin is a thermoplastic, a thermoset, or an elastomer.

15. The polymer compostion of claim 13 wherein said resin is a thermoplastic selected from the group consisting of polystyrene, polypropylene, polyethylene, polyvinyl chloride, and mixtures and copolymers thereof.

16. The polymer composition of claim 13 wherein said resin is a thermoset selected from the group consisting of unsaturated polyesters, epoxies, polyurethanes, and mixtures thereof.

17. The polymer composition of claim 13 wherein said resin is an elastomer selected from the group consisting of chlorinated polyethylene, styrene butadiene rubber, natural rubber, and mixtures thereof.

18. A fluoride dentifrice comprising:
   (a) about 30–98 wt. % of a vehicle having a pH of about 5–8;
   (b) about 2–70 wt. % alumina abrasive particles having an average particle size of about 1–20 microns, said particles being surface-treated by the method of claim 1; and
   (c) about 0.01–2 wt. % fluoride ion dissolved in the vehicle.

19. In a polymer composition comprising about 100 parts by weight of a polymeric resin, about 1–400 parts by weight alumina hydrate particles having average particle size of about 0.1–200 microns and about 5–50 parts by weight of a halogenated hydrocarbon, the improvement wherein said alumina hydrate particles are surface-treated by:
   (a) mixing the particles with an aqueous solution of a surface treating agent selected from the group consisting of
      (1) an alkali metal silicate at an initial pH of at least 8.5,
      (2) hydrogen peroxide,
      (3) an acid selected from the group consisting of hydrochloric acid, acetic acid, phosphoric acid, phosphonic acid and phosphinic acid,
      (4) an organophosphorous compound selected from the group consisting of organophosphonates having the formula $RPO(OH)_2$ wherein R is a $C_1$–$C_{30}$ hydrocarbon group, organophosphinates having the formula $RR'PO(OH)$ wherein R is as defined above and R' is hydrogen or a $C_1$–$C_{30}$ hydrocarbon group, $C_1$–$C_5$ alkyl esters of said organophosphonates and organophosphinates, phosphoric acid monoesters having the formula $ROPO(OH)_2$ and phosphoric acid diesters having the formula $R_2OPO(OH)$;
   (b) adjusting the pH of the aqueous solution to about 5–7;
   (c) separating the alumina hydrate particles from the solution; and
   (d) drying the surface-treated particles.

20. In a fluoride dentifrice comprising about 30–98 wt. % of a vehicle having a pH of about 5–8, about 2–70 wt. % alumina abrasive particles having average particle size of about 1–20 microns and about 0.01–2 wt. % fluoride ions dissolved in the vehicle, the improvement wherein said alumina particles are surface-treated by:
   (a) mixing the particles with an aqueous solution of a surface treating agent selected from the group consisting of
      (1) an alkali metal silicate at an initial pH of at least 8.5,
      (2) hydrogen peroxide,
      (3) an acid selected from the group consisting of hydrochloric acid, acetic acid, phosphoric acid, phosphonic acid and phosphinic acid,
      (4) an organophosphorous compound selected from the group consisting of organophosphonates having the formula $RPO(OH)_2$ wherein R is a $C_1$–$C_{30}$ hydrocarbon group, organophosphinates having the formula $RR'PO(OH)$ wherein R is as defined above and R' is hydrogen or a $C_1$–$C_{30}$ hydrocarbon group, $C_1$–$C_5$ alkyl esters of said organophosphonates and organophosphinates, phosphoric acid monoesters having the formula $ROPO(OH)_2$ and phosphoric acid diesters having the formula $R_2OPO(OH)$;
   (b) adjusting the pH of the aqueous solution to about 5–7;
   (c) separating the alumina hydrate particles from the solution; and
   (d) drying the surface-treated particles.

* * * * *

UNITED STATES PATENT AND TRADEMARK OFFICE
CERTIFICATE OF CORRECTION

PATENT NO. : 4,781,982
DATED : November 1, 1988
INVENTOR(S) : Lawrence L. Musselman, Larry F. Wieserman It is certified that error appears in the above-identified patent and that said Letters Patent is hereby corrected as shown below:

| | |
|---|---|
| Col. 1, line 37 | Change "luoride" to --fluoride--. |
| Col. 4, line 6 | After "was" insert --measured every hour using a fluoride-specific electrode. Results--. |
| Claim 15, Col. 5, line 29 | Change "compostion" to --composition--. |
| Claim 19, Col. 6, line 13 | Change "$C_1C_{30}$" to --$C_1$-$C_{30}$--. |

Signed and Sealed this

Fourth Day of April, 1989

Attest:

DONALD J. QUIGG

Attesting Officer

Commissioner of Patents and Trademarks